United States Patent [19]

Sandler

[11] Patent Number: 5,430,180
[45] Date of Patent: Jul. 4, 1995

[54] PREPARATION OF PROPANONE-1,3-DISULFONIC ACID

[75] Inventor: Stanley R. Sandler, Springfield, Pa.

[73] Assignee: Elf Atochem N.A., Inc., Philadelphia, Pa.

[21] Appl. No.: 197,373

[22] Filed: Feb. 16, 1994

Related U.S. Application Data

[63] Continuation of Ser. No. 924,116, Aug. 3, 1992, abandoned, which is a continuation of Ser. No. 434,614, Nov. 9, 1989, abandoned, which is a continuation-in-part of Ser. No. 44,933, May 1, 1987, abandoned.

[51] Int. Cl.$^6$ ........................................... C07C 309/05
[52] U.S. Cl. ................................................... 562/102
[58] Field of Search ......................................... 562/102

[56] References Cited

PUBLICATIONS

Gilbert Sulfonation and Related Reactions (1965) pp. 37–41.
Chem Abst. 45, 8445i (1951) Terentev et al.
J. Org Chem 30, 515–517 (1965) Grot.

*Primary Examiner*—Alan Siegel

[57] ABSTRACT

Propanone-1,3-disulfonic acid (acetone disulfonic acid) may be prepared by reacting chlorosulfonic acid with acetone preferably in the presence of a solvent for the reactants, such as methylene chloride, although a neat reaction is possible. The reactants and reaction conditions prior to separation should be substantially anhydrous, but water may be added after reaction to separate the product as an aqueous solution.

12 Claims, No Drawings

PREPARATION OF PROPANONE-1,3-DISULFONIC ACID

This is a continuation of application(s) Ser. No. 07/924,116 filed on Aug. 3, 1992, abandoned which is continuation of application Ser. No. 07/434,614 filed Nov. 9, 1989, abandoned, which is a continuation-in-part of application Ser. No. 07/044,933 filed May 1, 1987, abandoned.

FIELD OF THE INVENTION

The present invention is directed to methods for the preparation of propanone-1,3-disulfonic acid, also more commonly known as acetone disulfonic acid.

BACKGROUND OF THE INVENTION

Methods for preparation of propanone-1,3-disulfonic acid have been known for over thirty-five years, but these methods have a number of serious deficiencies.

An early reported method involved the reaction of acetone with dioxane-sulfur trioxide complex to yield acetone disulfonic acid, which was isolated as the barium salt, A. P. Terentev and L. A. Yanovskaya, *Doklady Akad. Nauk. S.S.S.R.*, 75,235 (1950); *Chem. Abstracts*, 45,8445i (1951) *Zh. Obshch. Khim.*, 23,618 (1953); *Chem. Abstracts*, 48,6958 (1954). This method has the disadvantage of requiring dioxane-sulfur trioxide, which is not commercially available on a large scale.

It was later reported that propanone-1,3-disulfonic acid could be prepared by the sulfonation of acetone with fuming sulfuric acid or oleum, W. Grot, *J. Org. Chem.*, 30,515 (1965) and German Patent 70,392 issued Jun. 28, 1968 to F. Wolf. This method has the disadvantage of requiring one to separate the product from a large excess of sulfuric acid. Another difficulty is the preparation of oleum from sulfuric acid and sulfur trioxide, which is difficult to handle due to its narrow liquid range (boiling point 44.8 degrees Centigrade, freezing point 17 degrees Centigrade), and trace amounts of water act as a polymerization catalyst for liquid sulfur trioxide, producing polymers having elevated boiling points. In addition, oleum is not stable, and the sulfur trioxide sometimes separates as a lower layer which is difficult to re-dissolve.

In the same reference cited above, Grot also made reference to another method (no citation given) for the preparation of propanone-1,3-disulfonic acid from 1,3-dichloroacetone and alkali sulfites. This method would have the disadvantage of requiring expensive 1,3-dichloroacetone and would give the disodium or dipotassium salts rather than the free acid. The disodium or dipotassium salts are rather difficult to convert to the free acid. The procedure used for preparing the dipotassium salt was described earlier by F. Raschig and W. Prahl, *Ber. der deutch. chem. Ges.*, 59B,2025 (1926).

U.S. Pat. No. 3,454,628 of G. Schroder et al discloses a method somewhat related to the Grot method described above. In the method of this patent acetone was reacted with fuming sulfuric acid in the presence of ammonium sulfate at 85 to 90 degrees Centigrade to directly prepare the diammonium salt of propanone-1,3-disulfonic acid. The free acid was not isolated from the salt, and this process also suffers from the same disadvantages as described above for the Grot process.

BRIEF SUMMARY OF THE INVENTION

According to the present invention a relatively simple method is provided for preparing propanone-1,3-disulfonic acid by reacting chlorosulfonic acid with acetone. The reaction is preferably carried out in the presence of a solvent, such as methylene chloride, for the reactants, and the precipitated product may be dissolved in water and separated from the solvent layer. Prior to the separation, the reaction should be under substantially anhydrous conditions.

DETAILED DESCRIPTION OF THE PREFERRED EMBODIMENTS

Propanone-1,3-disulfonic acid (acetone disulfonic acid) is prepared by reacting chlorosulfonic acid with acetone in the presence or absence of a solvent. The reaction may be represented by the following equation:

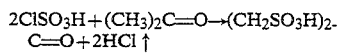

$$2ClSO_3H + (CH_3)_2C=O \rightarrow (CH_2SO_3H)_2C=O + 2HCl \uparrow$$

The reaction is exothermic and proceeds rapidly with only slight to moderate warming of the reaction mixture. The hydrogen chloride which is formed as a by-product is liberated during the reaction, and when its evolution ceases the reaction is complete.

The chlorosulfonic acid is preferably 99–100% grade, which is available commercially from several sources. The acetone is also available commercially and is preferably 100%, anhydrous grade. Since chlorosulfonic acid reacts vigorously with water, it is preferred that the reactants and the reaction conditions be substantially anhydrous. The primary impurities in the chlorosulfonic acid are hydrochloric and sulfuric acids, which form from contamination with water.

The reaction may be carried out neat or in the presence of a solvent for the reactants. The use of a solvent is preferred, since the neat reaction mixture is difficult to stir, and the product forms as a solid lump. The use of a solvent allows easier handling, better mixing and improves reaction rate.

The solvent may be virtually any inert solvent which readily dissolves both reactants. Examples of suitable solvents include methylene chloride, carbon tetrachloride, 1,1,1-trichloroethane (methylchloroform), chloroform, dioxane, acetonitrile, tetrahydrofuran, and ethyl ether. Other suitable solvents will be evident to those skilled in the art. A particularly preferred solvent is methylene chloride.

Although the order of addition of the reactants is not particularly critical, it has been found preferable to dissolve the acetone in the solvent and add the resulting solution slowly to the chlorosulfonic acid in the reaction vessel. For example, the acetone solution may be added over a period of about one hour. After warming of the mixture to accelerate the reaction, the solvent can be refluxed while the reaction proceeds for about three to four hours.

The reaction proceeds readily at substantially atmospheric pressure, preferably under a dry air atmosphere, with simple agitation (e.g., stirring). Noticeable precipitation occurs throughout the reaction, and the evolved hydrogen chloride gas may be captured by conventional means.

The reaction temperature of the process will generally be in the range of about 4 to 60 degrees Centigrade, and preferably about 4 to 40 degrees Centigrade, unless the reaction is carried out under pressure. The upper end of the temperature range is limited by the lowest boiling component of the reaction mixture. For example, where methylene chloride is the solvent, the reaction at atmospheric pressure would be carried out at its boiling point of 40 degrees Centigrade or below. Where a higher boiling point solvent such as carbon tetrachloride (boiling point 76 degrees Centigrade) is used, the boiling point of acetone (56 degrees Centigrade) becomes the temperature limiting factor.

The reactants are generally present in about stoichiometric amounts, or preferably with a slight stoichiometric excess of chlorosulfonic acid. In particular, the mole ratio of chlorosulfonic acid to acetone can range from about 2:1 to 2.3:1. A ratio of slightly less than 2:1 may also be acceptable due to the volatility and potential loss of some of the acetone. It is preferred that the amount of solvent be kept to a minimum, consistent with optimum mixing, handling and reaction conditions.

The white solid precipitate of propanone-1,3-disulfonic acid may be recovered by filtration or by dissolving in water. However, the solid product is highly hygroscopic and difficult to dry, so that filtration is not a preferred recovery method. When water is added to the completed reaction mixture, the product is isolated as an aqueous solution (free of solvent) which requires less time than filtration. Depending on the concentration the aqueous solution of product may have a greater density than the methylene chloride solvent and may be easily separated from the methylene chloride solvent which contains any unreacted acetone and chlorosulfonic acid. The product can be conveniently sold either as an anhydrous solid or more preferably as a 70% aqueous solution which does not require the expense of drying.

Since chlorosulfonic acid has a boiling point of 151–152 degrees Centigrade, it is easier to handle than sulfur trioxide used in prior art processes. Moreover, propanone-1,3-disulfonic acid is readily separated from methylene chloride and similar solvents for the reactants, and the use of such a solvent allows one to isolate the product as an aqueous solution. The process of the invention produces yields in excess of 75% of the desired product.

The present invention will now be illustrated in more detail by reference to the following specific, non-limiting examples. In the examples proton ($H^1$nmr) and carbon ($C^{13}$nmr) nuclear magnetic resonance and elemental analysis were used to identify the propanone-1,3-disulfonic acid. The solvents for the nmr analysis were deuterated dimethyl sulfoxide ($D_6$-DMSO) and deuterium oxide ($D_2O$), with methanol as the internal standard.

EXAMPLE 1

To a 500 ml 3-necked round-bottom flask equipped with a dry ice condenser, thermocouple in glass tube, mechanical stirrer, gas outlet, and dropping funnel was added 116.5 g (1.0 mole) of chlorosulfonic acid (99%). A solution of 29.1 g (0.5 mole) of acetone dissolved in 75 ml of methylene chloride was added dropwise at such a rate as to maintain the temperature below 20 degrees Centigrade. When the addition was complete, the clear homogeneous solution was warmed to reflux. A vigorous evolution of hydrogen chloride began at about 35 degrees Centigrade with refluxing of the methylene chloride. After 15 minutes reaction white solids began to precipitate, and the reaction continued for about another 3 to 3.5 hours. The white solid was either filtered under a nitrogen blanket and dried under reduced pressure or 109.0 g water was added and the 50% solution of product (bottom layer) was isolated.

The calculated yields were in the range of 75–100% of propanone-1,3-disulfonic acid. The proton nuclear magnetic reasonance ($H^1$nmr) and carbon 13 ($C^{13}$nmr) analyses indicated the following which were consistent with the structure of propanone-1,3-disulfonic acid:

| | Chemical Shifts (ppm) $D_2O$ Solvent |
|---|---|
| $H^1$ NMR | |
| Proton Assignment | |
| —$CH_2$— | 4.20 |
| HO— | 6.76 |
| $CH_3$—($CH_3OH$) | 3.30 (Standard) |
| $C^{13}$ NMR | |
| Carbon Assignment | |
| —$CH_2$— | 61.42 |
| $-\overset{\overset{O}{\|}}{C}-$ | 194.03 |
| $CH_3(CH_3OH)$ | 49.00 |

EXAMPLE 2

Example 1 was repeated under the same conditions of reaction, except no solvent was used and the temperature of the reaction was 14 to 50 degrees Centigrade (1-hour reaction time). The $H^1$ and $C^{13}$nmr analyses were as follows and were consistent with the structure of propanone-1,3-disulfonic acid:

| | Chemical Shifts (ppm) | |
|---|---|---|
| | $D_6$-DMSO Solvent | $D_2O$ Solvent |
| $H^1$ NMR | | |
| Proton Assignment | | |
| $CH_2$ | 3.92 | 4.34 |
| OH | 0.61 | 5.19 |
| $C^{13}$ NMR | | |
| Carbon Assignment | | |
| C=O | 195.82 | 196.18 |
| $CH_2$ | 64.45 | 63.50 |

The elemental analysis of the solid product was calculated as the monohydrate (very hygroscopic) of propanone-1,3-disulfonic acid:

| | Calcd. | Found |
|---|---|---|
| C | 15.25 | 15.6 |
| H | 3.39 | 3.21 |
| S | 27.12 | 28.2 |

EXAMPLE 3

Example 1 was repeated under the same conditions of reaction, except carbon tetrachloride was used as the solvent and the temperature range of reaction was 7 to 52 degrees Centigrade. The elemental analysis of the solid product was as follows:

| | |
|---|---|
| C | 15.7 |
| H | 2.96 |

| -continued | |
|---|---|
| S | 28.1 |

Propanone-1,3-disulfonic acid has utility as an alkylation and esterification catalyst, as a solubility enhancer for dimethyl disulfide in concentrated hydrochloric acid solutions, as an electrochemical stripping agent for various metals, as a solvent for various metals by forming water soluble salts some of which are useful transesterification catalysts, as a reactant for forming polymers by undergoing aldol or ketone condensations (e.g., reactions with formaldehyde, glyoxal, phenol-formaldehyde, ketal formation, hydrazine reactions, photochemical condensations, bisulfite reactions, etc.), and as an additive to enhance flame retardancy when using the salts (e.g., ammonium salts).

The present invention may be embodied in other specific forms without departing from the spirit or essential attributes thereof, and accordingly, reference should be made to the appended claims, rather than the specification, as indicating the scope of the invention.

I claim:

1. A method for preparing propanone-1,3-disulfonic acid comprising reacting chlorosulfonic acid with acetone in the presence of a chlorinated organic solvent for the reactants and directly isolating free propanone-1,3-disulfonic acid from the reaction mixture by (a) separating the free disulfonic acid precipitate from said solvent or (b) adding salt-free water to said reaction mixture to form aqueous and solvent layers, and separating the aqueous layer consisting essentially of dissolved free disulfonic acid, from the solvent layer.

2. The method of claim 1 wherein the reaction is carried out in the presence of a chlorinated hydrocarbon solvent for the reactants.

3. The method of claim 1 wherein said solvent is methylene chloride, carbon tetrachloride, 1,1,1-trichloroethane, or chloroform.

4. The method of claim 2 wherein said solvent is methylene chloride.

5. The method of claim 1 wherein the reactants are substantially anhydrous.

6. The method of claim 1 wherein the reaction is carried out at a temperature of about 4° to about 60° C.

7. The method of claim 1 wherein the reaction temperature range is about 4° to about 40° C.

8. The method of claim 1 wherein the reactants are present in about stoichiometric amounts to a slight stoichiometric excess of said chlorosulfonic acid.

9. The method of claim 1 wherein the acetone is first dissolved in said solvent and the resulting solution is added to said chlorosulfonic acid.

10. The method of claim 9 wherein the reaction mixture is warmed after addition of the acetone to said chlorosulfonic acid until vigorous evolution of hydrogen chloride occurs.

11. The method of claim 1 wherein said solvent is refluxed during the reaction.

12. The method of claim 1 wherein the reaction is carried out under anhydrous conditions at atmospheric pressure.

* * * * *

UNITED STATES PATENT AND TRADEMARK OFFICE
CERTIFICATE OF CORRECTION

PATENT NO. : 5,430,180
DATED : July 4, 1995
INVENTOR(S) : Stanley R. Sandler

It is certified that error appears in the above-indentified patent and that said Letters Patent is hereby corrected as shown below:

Col. 6, line 15, claim 7 should read as follows:

7. The method of claim 6 wherein the reaction temperature range is about 4° to about 40° C.

Signed and Sealed this

Nineteenth Day of September, 1995

Attest:

BRUCE LEHMAN

Attesting Officer

Commissioner of Patents and Trademarks